United States Patent [19]

Becker et al.

[11] Patent Number: 5,169,386

[45] Date of Patent: * Dec. 8, 1992

[54] METHOD AND CATHETER FOR DILATATION OF THE LACRIMAL SYSTEM

[75] Inventors: Bruce B. Becker, 17974 Boris Dr., Encino, Calif. 91316; William A. Berthiaume, Hudson, Mass.

[73] Assignee: Bruce B. Becker, Encino, Calif.

[*] Notice: The portion of the term of this patent subsequent to Jun. 4, 2008 has been disclaimed.

[21] Appl. No.: 542,598

[22] Filed: Jun. 25, 1990

Related U.S. Application Data

[63] Continuation-in-part of Ser. No. 405,766, Sep. 11, 1989, Pat. No. 5,021,043.

[51] Int. Cl.$^5$ ............................................. A61M 31/00
[52] U.S. Cl. .................................... 604/49; 604/96; 606/192; 128/658
[58] Field of Search .................... 128/658, 656–657; 604/96–103, 264–265, 270, 281–282, 49; 606/192, 194

[56] References Cited

U.S. PATENT DOCUMENTS

| | | | |
|---|---|---|---|
| 4,771,776 | 9/1988 | Powell et al. | 606/194 |
| 4,777,951 | 10/1988 | Cribier et al. | 606/194 |
| 4,920,980 | 5/1990 | Jackowski | 128/658 X |
| 4,921,478 | 5/1990 | Solano et al. | 604/53 |
| 4,943,275 | 7/1990 | Stricker | 600/18 |
| 5,021,045 | 6/1991 | Buckberg et al. | 604/102 X |

*Primary Examiner*—C. Fred Rosenbaum
*Assistant Examiner*—C. Maglione
*Attorney, Agent, or Firm*—Charles H. Schwartz; Ellsworth R. Roston

[57] ABSTRACT

A dilation catheter having an inflatable member and an element for retaining a curved shape, and a method of using same to restore patency to an obstructed portion of the lacrimal system. The catheter is inserted into the lacrimal system and the inflatable member is positioned in the obstructed portion. Insertion of the catheter is facilitated by mechanically imparting a curved shape to a distal portion of the catheter. The inflatable member is inflated to dilate the obstructed portion to restore patency to the lacrimal system. Preferably, the catheter includes one or more visually perceivable markers having a known spaced relationship to one of the ends of the inflatable member. Positioning of the inflatable member is assisted by aligning the marker relative to an opening into the lacrimal system.

46 Claims, 6 Drawing Sheets

METHOD AND CATHETER FOR DILATATION OF THE LACRIMAL SYSTEM

RELATED CASE

This application is a continuation-in-part application of U.S. Ser. No. 07/405,766, Becker et al., Method and Catheter for Dilatation of the Lacrimal System, filed Sep. 11, 1989, now U.S. Pat. No. 5,021,043.

FIELD OF THE INVENTION

This invention relates to an improved method of restoring patency to an obstructed portion of the lacrimal system using a dilatation catheter having a selected curve imparted to its distal end, and to such a catheter which includes material for retaining the selected curve to facilitate insertion through the lacrimal system.

BACKGROUND OF THE INVENTION

The excessive overflow of tears down a cheek due to an obstruction in the nasolacrimal drainage system is a relatively common problem. The excessive overflow, referred to as epiphora or "watering eye", is often accompanied by infection with attendant inflammatory reaction.

Normally, tears are drained from the eye through the nasolacrimal drainage system (hereinafter the lacrimal system) which includes an upper and lower canaliculus, each of which communicates with its respective eyelid through an opening known as the punctum. The other ends of the canaliculi join together the common canaliculus which then enters the lacrimal sac. The tears then drain through the lacrimal sac into the upper end of the nasolacrimal duct. The lower end of the nasolacrimal duct opens into the nose.

Presently, minor obstructions of the lacrimal system commonly are treated by dilatation using metal probes in children. In adults obstructions of the nasolacrimal duct are treated by performing a dacryocystorhinostomy (DCR), during which the lacrimal sac is surgically connected with the nasal cavity. DCR is a relatively major surgical procedure involving making an incision next to the bridge of the nose near the lacrimal sac, breaking through the bone to access the nose, and cutting away a portion of the lacrimal sac. The newly created opening into the nose is referred to as the ostium. In children who do not respond to probing or placement of silicone tubes in the lacrimal system a DCR is performed.

As many as one in ten DCR operations fail due to subsequent closure of the ostium. The ostium can be reopened surgically, but few patients wish to undergo the trauma of a second surgery which involves the excising of additional tissue, anesthesia, and subsequent packing of the nose with absorbent material for two to three days following the surgery.

A number of techniques presently are attempted to avoid the trauma of a second surgery. Dilatation of the ostium with a metal probe, intranasal dilatation with a muscle hook, and dilatation with a knotted suture are used with varying degrees of success. A silicone tube frequently is attached to the probe so that the silicone tubing is installed in the lacrimal system to serve as a stent in an attempt to maintain patency of the ostium. However, the canaliculus is typically only 0.5-1.0 mm in diameter and the internal diameter of the stent is therefore relatively small and ineffective. These techniques usually do not succeed in reopening the ostium for a sufficient period of time. Often, the tissue surrounding the ostium simply recloses after the probe is removed, even when the silicone tubing stent is present.

One such stent is a silicone catheter with an inflatable balloon which is positioned within the patient's lacrimal sac. The catheter maintains communication between the lacrimal sac and the nose. The balloon is of a sufficient size to prevent postoperative migration of the catheter to the nasal fossa. After the patient is healed, the balloon is deflated and the catheter is removed by pulling it through the patient's nostril. In other words, the balloon is not used for dilatation, but simply serves as a retaining element for the stent.

Obstruction of a canaliculus can also occur. Various solid, rigid instruments have been used to dilate a canalicular stenosis. Commonly, a rigid metal probe is used followed by silicone intubation as a stent. However, the number of failures is high and an operation called a conjunctivodacryocystorhinostomy (CDCR) must frequently be performed. The CDCR involves bypassing the lacrimal system by surgically creating an opening from the eye into the nose. A short pyrex tube is then installed so that it creates a passage from the eye straight into the nose. This procedure is poorly tolerated by most patients. Further, the CDCR can become obstructed, particularly if the pyrex tube becomes dislodged.

Additionally, obstruction of the punctum is very common. Again, the punctal stenosis is usually treated with a solid metal probe with varying degrees of success.

A novel method of treating lacrimal obstructions is described in Becker et al., "Balloon Catheter Dilatation in Lacrimal Surgery", Opthalmic Surgery 20:193-198 (March, 1989). The article describes balloon dilatation of four patients with failed DCR. A standard Bowman probe was inserted through the canaliculus and lacrimal sac and advanced through the nasal ostium into the nose. The metal probe was removed, and a 0.014 inch diameter guide wire was advanced along the same path. The distal end of the guide wire was grasped by a hemostat in the nose and pulled outwardly from the nose. A USCI Profile Plus 4.0 mm coronary balloon catheter, having a deflated profile of 0.042 inch and a balloon length of 20 mm, was guided over the wire. An ink mark previously placed on the catheter shaft proximal to the proximal end of the full-diameter region (center region) of the balloon was aligned with the punctum. The balloon was located in the lacrimal sac and extended through the ostium into the nose, and the ink mark was aligned with the punctum. Two dilatations were performed at 10 bar inflation pressure. The guide wire and balloon then were withdrawn.

The technique disclosed by Becker et al. is useful, but involves a number of time consuming steps including the insertion of a guide wire through the lacrimal system, and then separately advancing the balloon catheter over the guide wire. It would be desirable to utilize fewer steps in treating obstructions within the lacrimal system, and to use a procedure which is similar to the use of opthalmic probes with which opthamologists are familiar.

In a separate subject area, balloon catheter dilatation has been used to treat stenotic blood vessels, urinary tract obstructions, and strictures of the gastrointestinal tract. In percutaneous transluminal coronary angioplasty, for example, a guide wire is maneuvered along a selected coronary artery until an occlusion is reached. A balloon catheter is then advanced over the guide wire by pushing on the proximal end of the balloon catheter. After the balloon is positioned within the occlusion, it is inflated to dilatate the occlusion. Frequently, the first balloon catheter is withdrawn and a second, larger-diameter balloon catheter is positioned to perform a subsequent dilatation. No suggestion has been made, other than the Becker et al. 1989 article, to use balloon catheters in the treatment of an obstructed lacrimal system by performing dilatation of the obstruction.

SUMMARY OF THE INVENTION

In the present invention, a dilatation catheter is provided which simulates the stiffness and flexibility of an opthalmic probe. The catheter has sufficient column strength and resistance to lateral bending, yet also has sufficient flexure to follow the contours of the lacrimal system. Preferably, the catheter includes an element which retains a curved shape after sufficient mechanical force is applied to the element, for example by grasping a distal portion of the catheter with two hands and bending the catheter to form a curve. The curved shape facilitates insertion of the catheter through the lacrimal system to access an obstructed portion of the system. An inflatable member carried by the catheter can then be inflated to dilate the obstructed portion. The catheter is sufficiently stiff to enable insertion in the same manner as an opthalmic probe, yet is as flexible as a probe to minimize trauma to the lacrimal system. No separate guide wire is required for insertion. Use of this catheter obviates the need for surgery with its attendant trauma.

The curve retention element may be a metal wire which is carried by a distal portion of the catheter. The main body of the catheter may define an inflation lumen having a distal opening which communicates with the inflatable member to enable inflation and deflation of the inflatable member. The wire lies within a distal portion of the inflation lumen without occluding the lumen. The wire is attached to the catheter body distal to the distal opening of the inflation lumen. In one embodiment, the catheter body is a hollow stainless steel tube, the curve retention element is a stainless steel wire, and the distal end of the catheter includes a rounded distal tip formed of cured adhesive.

It is also desirable for the catheter to include a lubricious coating. This facilitates insertion of the catheter into the lacrimal system. The coating may be a silicone coating bonded to the catheter, or may be topically applied to the catheter body and the inflatable member.

The dilatation catheter of the invention preferably has one or more visually perceivable markers having a known spaced relationship from one of the distal end and the proximal end of the center region of the inflatable member. These markers enable alignment of the inflatable member with the obstructed portion of the lacrimal system to be dilated. The catheter preferably also includes a visually perceivable marker having a known spaced relationship to one of the ends of the inflatable member. Positioning the inflatable member includes aligning the marker relative to an opening in the lacrimal system, such as a punctum, the opening of the nasolacrimal duct into the nose, or an ostium formed between the nose and the lacrimal sac. The arrangement of the markings and the technique of utilizing the markings varies according to the location of the obstructed portion to be dilated. For treating a failed dacryocystorhinostomy (DCR), for example, a catheter according to the invention includes a first visually perceivable marker spaced 9-13 mm proximal to the proximal end of the center region such that when the catheter is inserted through a punctum and associated canaliculus and then through an ostium formed between the nose and the lacrimal sac, the first marker is aligned relative to the punctum to position the inflatable member. Preferably, the inflatable member is a translucent balloon and a second visually perceivable marker is located beneath the balloon at a distance of 0-6 mm distal to the proximal end of the center region to enable alignment of the second marker relative to the ostium. Alternatively, the catheter is inserted through the ostium and then through the canaliculus and its associated punctum, the first visually perceivable marker is spaced 9-13 mm distal to the distal end of the center region, and a second visually perceivable marker is located beneath the balloon at a distance of 0-6 mm proximal to the distal end of the center region. The first marker is aligned relative to the punctum and the second marker is aligned relative to the ostium to position the balloon to effectively dilate the ostium.

To dilate the nasolacrimal duct, the catheter is inserted through a punctum and associated canaliculus into the lacrimal sac, and then advanced through the nasolacrimal duct. A first visually perceivable marker is located beneath the inflatable member at a distance of 0-6 mm proximal to the distal end of the center region for alignment of the first marker relative to the opening of the nasolacrimal duct into the nose. A second visually perceivable marker is spaced 9-16 mm proximal to the proximal end of the center region for alignment relative to the punctum. The second marker is preferably located 9-11 mm from the proximal end of the center region. The catheter further includes a third marker located 14-16 mm proximal to the proximal end of the center region. The second and third markers are then aligned relative to the punctum. If the balloon is not sufficiently long to occupy the entire nasolacrimal duct, a first dilatation is performed after the first marker is aligned relative to the opening of the nasolacrimal duct. Thereafter, a second dilatation is performed after aligning the second and third markers relative to the punctum after the catheter is withdrawn toward the canaliculus.

During yet another procedure according to the invention, the catheter is inserted through a punctum and associated canaliculus for dilatation of the canaliculus. A first visually perceivable marker is spaced 9-16 mm proximal to the distal end of the center region for alignment relative to the punctum. The catheter and method according to this invention can also be used for dilatation after conjunctivodacryocystorhinostomy (CDCR) and for dilatation of the punctum. These techniques provide successful dilatation without the need for surgery and its potential complications. The methods according to the invention can be used to restore patency to a failed surgical procedure, or can be used as a primary treatment to treat the obstruction without requiring any surgery.

It is therefore an object of the invention to provide an improved dilatation catheter for use in the treatment of obstructed lacrimal ducts.

A further object of the invention is to provide such a catheter having one or more visually perceivable markers which readily enable alignment of an inflatable member with the obstruction.

Yet another object of the invention is to provide such a catheter which is similar in stiffness and flexibility to an opthalmic probe.

A still further object of the invention is to provide such a catheter which can be bent and manipulated like an opthalmic probe.

A further object of the invention is to provide such a catheter which does not require use of a guide wire.

It is a further object of this invention to provide an easier, more effective procedure for restoring patency to an obstructed lacrimal system.

Yet another object of this invention is to provide a less traumatic technique for correcting a failed DCR, and a less invasive primary treatment as an alternative to DCR.

A still further object of the invention is to provide such a technique which avoids surgery and reduces trauma to the patient.

DESCRIPTION OF THE DRAWINGS

The foregoing and other objects and advantages of the invention will be appreciated more fully from the following further description thereof with reference to the accompanying drawings wherein:

FIG. 9a is a schematic cross-sectional view of the dilatation catheter shown in FIG. 8;

FIG. 9b is a more detailed enlargement of the distal portion of the dilatation catheter shown in FIG. 9a; and FIG. 10 is a schematic view of the dilatation catheter of FIG. 8 after it is bent to facilitate insertion through the lacrimal system.

DESCRIPTION OF THE ILLUSTRATIVE EMBODIMENT

According to the present invention, an improved dilatation catheter is provided as shown below in FIGS. 8-10. This dilatation catheter is used in a similar manner as described in the parent application in relation to FIGS. 1-7, with the additional advantage that the improved dilatation catheter according to the present invention includes an element for retaining a curved shape imparted to it by an opthomologist to facilitate insertion through the lacrimal system. Further, the catheter has a stiffness (both columnar and flexural) similar to that of an opthalmic probe and, therefore, can be inserted by itself without using a guide wire.

Dilatation by a method according to the invention of an obstruction in the nasolacrimal drainage system, hereinafter the lacrimal system, can be accomplished without surgery by providing a catheter having an inflatable member, inserting the catheter into the lacrimal system, and positioning the inflatable member proximal to and through the obstructed portion of the lacrimal system. The inflatable member is then inflated to dilate the obstructed portion to restore patency to the lacrimal system. This technique accomplishes much greater dilatation than that possible using a metal probe, a muscle hook, a knotted suture, or other attempts to restore patency without involving surgery.

The dilatation catheter and method according to the invention can be used to restore patency to the ostium formed between the nose and the nasolacrimal sac after a failed dacryocystorhinostomy (DCR), or for treating obstructions of the nasolacrimal duct, the canaliculus, the punctum, or combinations thereof within the lacrimal system.

The dilatation catheter and method provide an advantageous technique for accessing the lacrimal system through openings which are quite small. The punctum typically has an internal diameter of 0.5 mm and a length of approximately 1 mm. A canaliculus typically has a diameter of 0.5 mm in a relaxed, unexpanded state and a length of 10-12 mm. The artificial ostium formed during surgery usually has a diameter of approximately 2 mm and a length of 2 or more mm. The nasolacrimal duct is approximately 17 mm in length and has an inner diameter of 0.5-1 mm. The maximum diameter of the nasolacrimal duct is established by the diameter of the bone passageway, which is typically 3-4 mm in diameter.

Figure 1:
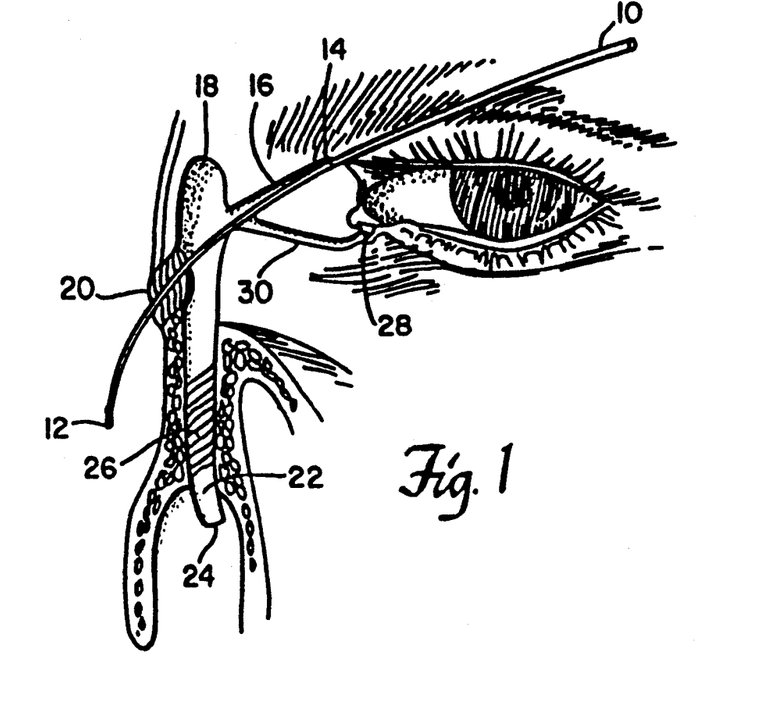
FIG. 1 is a schematic, partial, cross-sectional view of a patient with an obstructed nasolacrimal duct and an obstructed ostium through which a metal probe is passed during the method of the invention.
Figure 2:
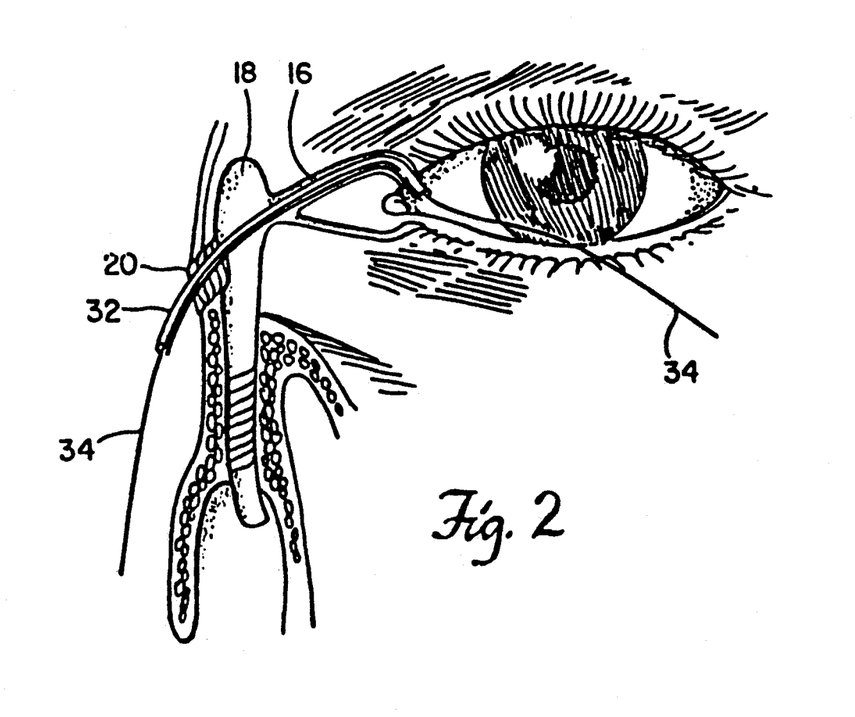
FIG. 2 is a similar view showing an angiocath sleeve and guide wire positioned within the lacrimal system.
Figure 3:
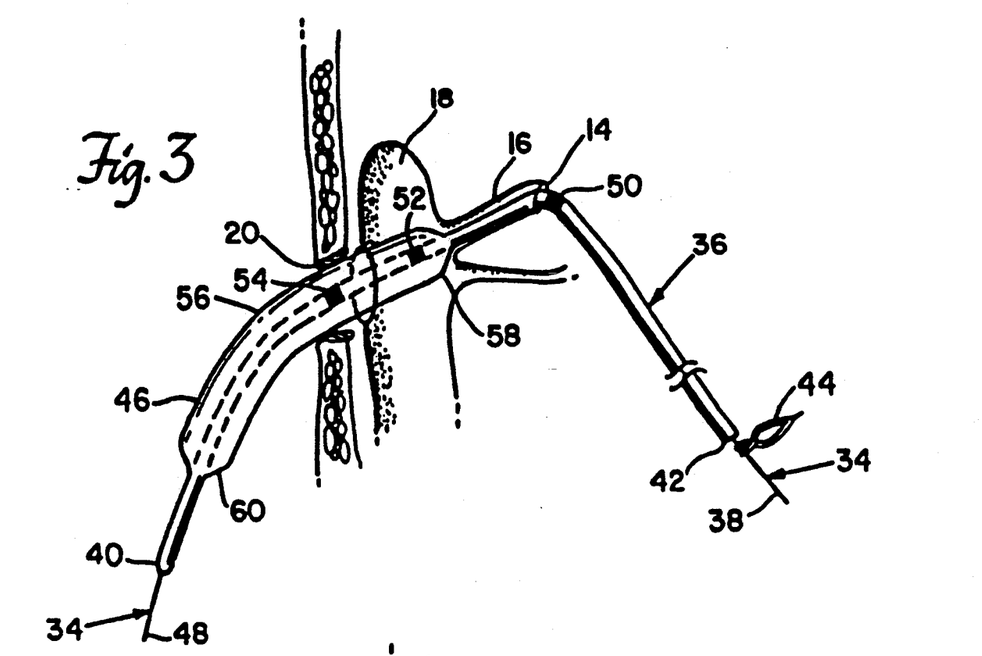
FIG. 3 is a schematic representation of the alignment of a dilatation catheter with features of the lacrimal system.

Dilatation of an ostium after a failed DCR is illustrated in FIGS. 1-3. Preferably, irrigation and postoperative dye testing are performed after the failed DCR and before and after catheter dilatation to confirm the need for dilatation and the success of the procedure. Postoperative dye testing can be performed by placing 2% fluorescein dye in the eye and examining the nose for presence of dye.

The patient is prepared before the dilatation procedure by applying a combination of topical and infiltration anesthesia. For example, topical 0.5% proparacaine is applied to the eye, and topical 4% lidocaine and 0.5% phenylephrine spray is delivered to the nose. A nerve block may be delivered to the anterior ethmoidal and infratrochlear nerves by injecting a 50:50 mixture of 2% lidocaine and 0.5% bupivicaine through the medial orbit. Oral or intravenous sedation may also be used.

Preferably, the insertion of a dilatation catheter according to the invention is preceded by a probe 10, such as the metal rod shown in FIG. 1. The probe 10 is approximately 0.5 mm (0.02 inch) in diameter and is moderately flexible. The distal end 12 of the probe 10 is inserted into the upper punctum 14 and passed through the upper canaliculus 16 into the lacrimal sac 18. The distal tip 12 is then inserted through the occluded ostium 20 and into the nose. The ostium was previously established during a DCR in an attempt to provide an alternative path for the drainage of tears because the normal path through the nasolacrimal duct 22 and its opening 24 into the nose is blocked by occlusion 26.

The probe 10 is alternatively advanced through lower punctum 28 and its associated lower canaliculus 30. In either case, use of the probe 10 allows the physician to determine the optimal insertion angle and proper maneuvering required to pass through the occluded ostium 20.

The probe is then withdrawn and a sleeve 32 is inserted as shown in FIG. 2. One such sleeve is a 20 gauge angiocath available from Deseret Medical, Inc. The angiocath has a sleeve formed of Teflon which is approximately 2 inches long and 1.1 mm (0.043 inch) in diameter. This angiocath further includes a metal core whose tip is cut and filed until it is blunt and flush with the end of the sleeve. The sleeve 32 is passed through the canaliculus 16, the lacrimal sac 18, and the ostium 20 in the same fashion as the probe. The sleeve 32 is visualized through the nose and is positioned such that there is a 5-10 mm clearance between it and the nasal septum. The metal core is withdrawn.

A guide wire 34 is then threaded through the sleeve 32 and into the nose. The guide wire 34 is drawn out of the nose by engaging it with a small muscle hook, or grasping it with a hemostat to bring it out through the external nare. The sleeve 32 is then withdrawn while leaving the guide wire in place. Use of the sleeve 32 is optional, but is desirable when passing through a very narrow obstruction through which the guide wire alone cannot readily be advanced. A preferred guide wire is the "Hyperflex" guide wire, catalog no. 004795 available from USCI, a division of C. R. Bard, Inc. This guide wire has a diameter of 0.36 mm (0.014 inch) and is coated with a silicone "Propel" coating.

After the guide wire 34 is installed and the sleeve 32 is withdrawn, a catheter 36 is advanced over the distal end 38 of the guide wire 34 until the distal end 40 of the catheter 36 is positioned near the punctum 14. The catheter 36 is then interlocked with the guide wire 34 near the proximal end 42 of the catheter 36 by clamping a hemostat 44 onto the guide wire 34. The hemostat 44 is a standard mosquito hemostat such as available from the V. Mueller Company. The inflatable member 46, in a deflated condition, is drawn into the lacrimal system by pulling on the distal end 48 of the guide wire 34. In other words, instead of pushing on the proximal end 42 of the catheter 36 to advance it into position, as is done during conventional angioplasty, the catheter is drawn into position by pulling on the guide wire.

The dilatation catheter 36 includes visually perceivable markers 50, 52, and 54 which assist in the positioning of the inflatable member 46. The markers 50, 52, and 54 are established by permanent indelible ink which is placed directly on the exterior of the shaft of the catheter 36. The inflatable member 46 is translucent so that the markers 52, 54 which underlie the balloon can be seen. The term "translucent" is intended in its broadest sense to cover both translucent and transparent materials such that the markers can be seen through the inflatable member. One such translucent material is polyethylene terephthalate. Other acceptable materials are polyvinyl chloride or Surlyn, both of which are also translucent materials. The inflatable member 46 is a balloon 3-6 mm in diameter and 5-10 mm in length, preferably 3.5-5.5 mm in diameter and 6-8 mm in length, for use to expand the ostium 20, although a longer balloon is acceptable as shown for the inflatable member 46, FIG. 3, which is approximately 20 mm in length. One such balloon catheter is the "Miniprofile" catheter, catalog no. 006480 available from USCI, having a 3.5 mm diameter balloon which has a deflated profile of 0.94 mm (0.037 inch).

The inflatable member 46 has a center region 56 which is the full-diameter region upon inflation. The proximal end of the center region 56 is attached to tapered proximal portion 58 and the distal end of the center region 56 is attached to a tapered distal region 60. The marker 52 is aligned with the proximal end of the center region 56, and the marker 54 is spaced 4-6 mm, preferably 5 mm, distal to the end marker 52. The catheter shaft is illustrated extending within the inflatable member 46 by dashed lines. The marker 50, referred to as an insertion or exit marker, is located 9-13 mm, preferably 10 mm, proximal to the end marker 52. The insertion marker 50 is aligned relative to the punctum 14 and the inflation marker 54 is aligned relative to the ostium 20. The inflation member 46 is then inflated to approximately ten bars pressure while the physician maintains proximal tension on the catheter 36 to inhibit the catheter from slipping into the nose. Preferably, the inflation member 46 first is partially inflated to two bars pressure and the catheter 36 is pulled proximally to place the proximal tapered region 58 at the junction of the lacrimal sac 18 and the upper canaliculus 16 before inflation to ten bars. Dilatation at ten bars pressure is performed for 5-15 minutes, preferably two times for ten minutes each.

Any discomfort experienced with the initial dilatation usually dissipates within a few seconds. Persistent pain may indicate that a portion of the center region 56 is within the canaliculus 16 and the inflatable member 46 should be advanced distally. After dilatation, the catheter 36 and the guide wire 34 are withdrawn. Topical antibiotic, steroid eye drops are given for approximately one week following the procedure.

Figure 4:
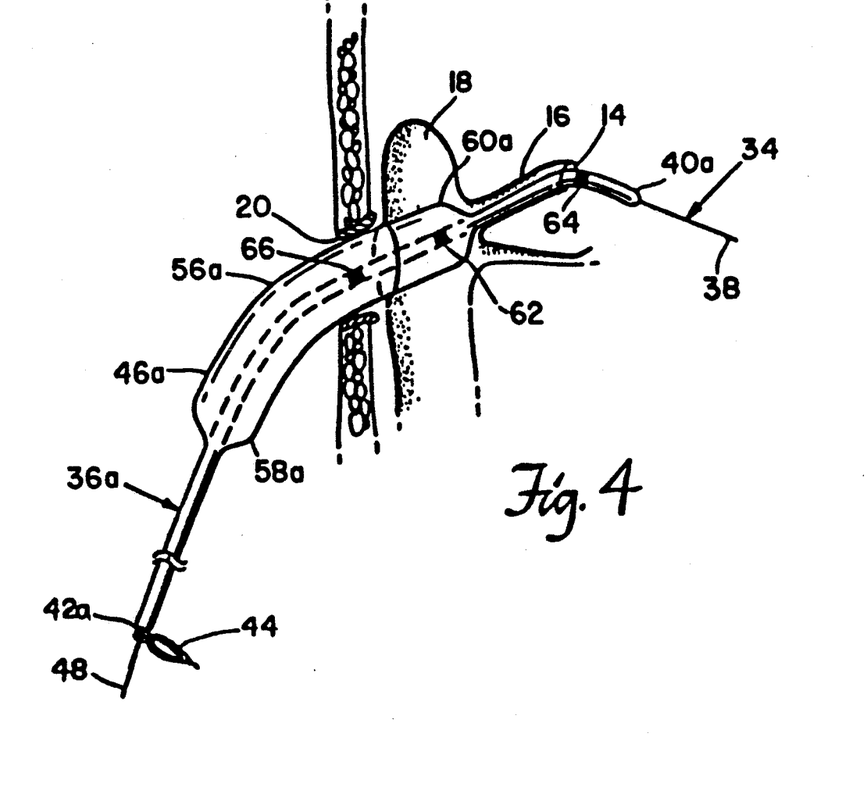
FIG. 4 is a schematic view of an alternative method in which the catheter is pulled into the lacrimal system through the nose.

Instead of bringing the dilatation catheter through the punctum to emerge through the ostium to the nose, the catheter can be advanced in the opposite direction as shown in FIG. 4. This "retrograde" technique is particularly useful when a larger-diameter balloon is required which cannot be advanced through the canaliculus. The dilatation catheter 36a is inserted over the distal end 48 of the guide wire 34 until the distal end 40a of the catheter 36a is positioned proximate to the ostium 20. A hemostat 44 is then clamped to the guide wire 34, and the proximal end 38 is pulled to draw the catheter 36a through the lacrimal sac 18 and the canaliculus 16 with its associated punctum 14. The boundary between the center region 56a and the distal tapered region 60a is indicated by end marker 62. Insertion marker 64 is placed 9-13 mm distal to the marker 62, and preferably at a distance of 10 mm. An additional inflation marker 66 is placed 4-6 mm, preferably 5 mm proximal to the end marker 62. The distal tapered region 58a lies within the nose. Dilatation is performed using inflatable member 46a as described above in relation to FIG. 3.

Figure 5A:
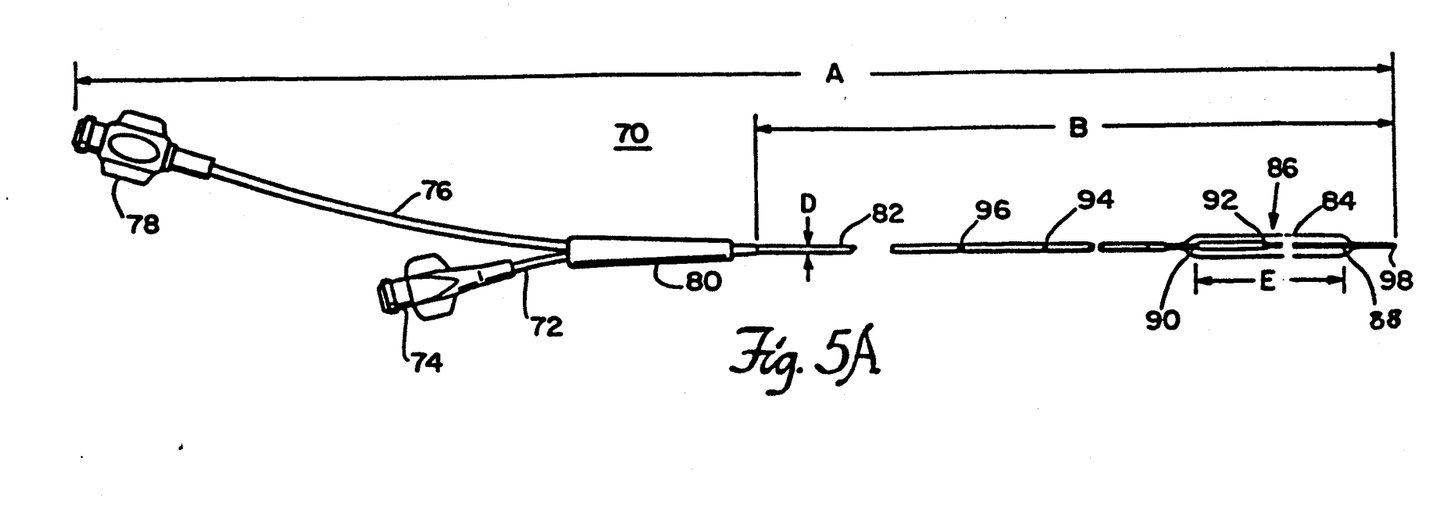
FIG. 5A is a schematic view of a dilatation catheter for use in the lacrimal system.

A schematic view of a dilatation catheter for use in the lacrimal system is shown in FIG. 5A. The catheter 70 is a two-lumen catheter having an inflation lumen accessed through leg 76 terminating in luer fitting 78 and a center lumen through which a guide wire may be passed, accessed through leg 72 which terminates in luer fitting 74. The catheter 70 has an overall length A of 62 cm±5 cm and a length B distal to sleeve 80 of 46 cm±2.5 cm. The main shaft 82 has a diameter D of 0.044 inch and is preferably made of high density polyethylene. The center region 84 of the balloon 86 has a diameter when inflated of 4.0 mm at 5 bars pressure and a length E of 8 mm which is indicated at both the distal and proximal ends by distal marker 88 and proximal marker 90, respectively. Inflation marker 92 is located approximately midway between markers 88 and 90. The catheter 70 further includes proximal insertion markers 94 and 96 which are located approximately 10 mm and 15 mm proximal to the proximal marker 90. The distal tip 98 of the catheter 70 has an outer diameter of approximately 0.68 mm (0.027 inch).

Figure 5B:
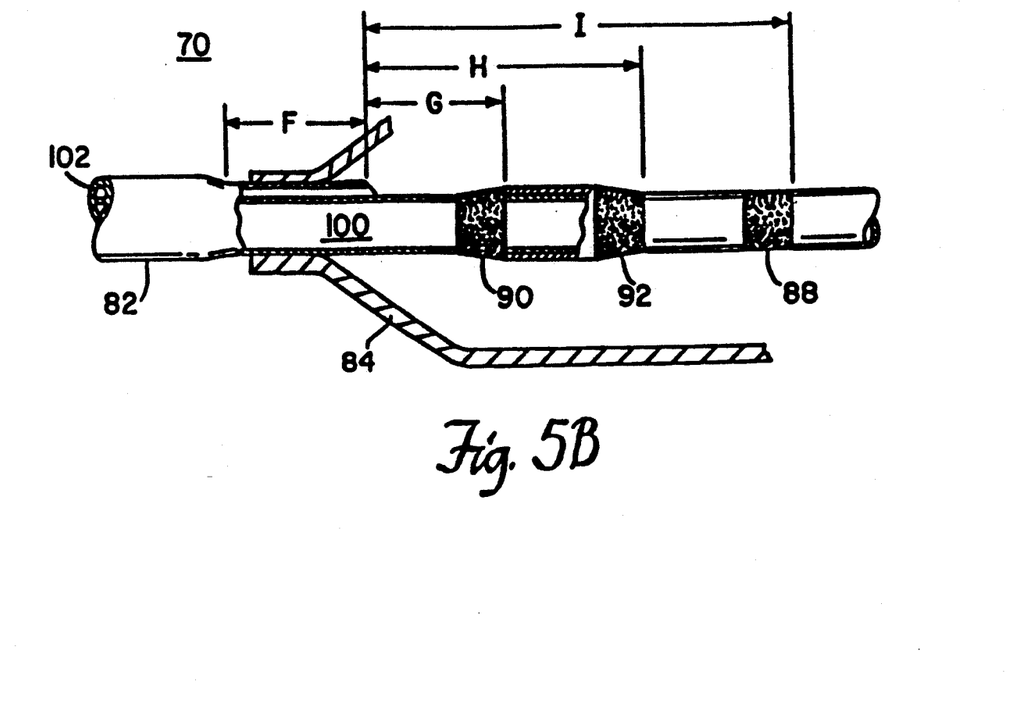
FIG. 5B is an enlarged view of the visually perceivable markings underlying the balloon.
Figure 6:
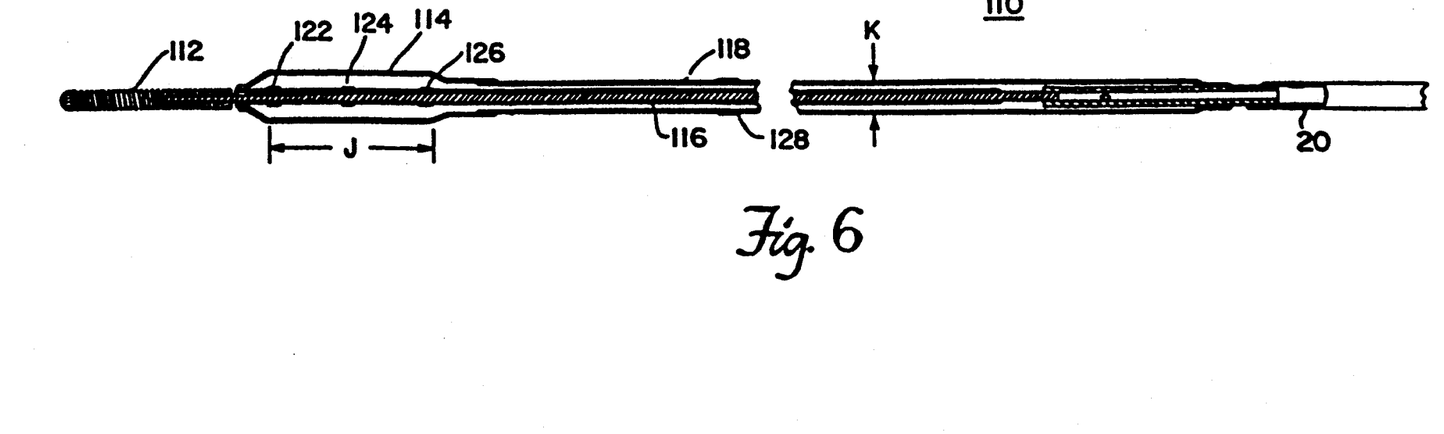
FIG. 6 is a schematic view of an alternative dilatation catheter for use in the lacrimal system which does not require a separate guide wire.

A portion of the distal end of the catheter 70 is shown in greater detail in FIG. 5B. The center lumen 100 and balloon inflation lumen 102 of shaft 82 are illustrated in partial cross-section. Dimension F indicates a reduced-diameter region at which the proximal end of the balloon 84 is attached, and dimensions G, H and I indicate the distal end of the markers 90, 92, and 88, respectively. In one embodiment, dimension F is 5.5 mm±1 mm, dimension G is 3.5 mm±1 mm, dimension H is 7.5±1 mm, and dimension I is 11.5 mm±1 mm. The markers 90, 92, and 88 are 1-1.5 mm wide bands of black permanent indelible ink such as Marabu TPU-73 pad printing ink. The ink is mixed with Marabu TPU-H ink hardener at a ratio of 4:1 and then roll printed on the shaft before the balloon 84 is placed over the shaft. Except for the shorter length of the balloon 84 and the presence of the visually perceivable markers, the catheter 70 is similar to the "Miniprofile" percutaneous transluminal coronary angioplasty catheter, catalog no. 006480 of USCI. As with the Miniprofile catheter, the shaft is preferably a high density polyethylene.

An alternative catheter according to the invention does not require a separate guide wire. A dilatation catheter 110, FIG. 6, includes 0.014 inch diameter spring coil tip 112, balloon 114, core wire 116, distal outer shaft 118, and proximal shaft 120. The core wire 116 establishes a distal segment which is more flexible than the remaining, proximal segment of the catheter 110. As described below in relation to FIGS. 8-10, a catheter according to the present invention preferably has a stiffer distal portion. The distal tapering of the core wire 116 and the helical coils of tip 112 provide greatest flexibility at the distal end of the distal segment to emulate a guide wire. This construction is similar to the catheter in U.S. Ser. No. 303,908, filed Jan. 30, 1989, assigned to C. R. Bard, Inc. and incorporated herein by reference. In this construction, however, the balloon 114 is 4.0 mm±0.2 mm in diameter and 8.0±1 mm in length. The distal end marker 122, center marker 124, proximal marker 126, and proximal insertion marker 128 are shown as raised for clarity, but again are indelible ink bands applied to the catheter structure, in this example core 116 and outer shaft 118, respectively. The spacing of the markers 122-128 are as described above in FIGS. 5A-5B for dilatation of an ostium after a failed DCR, and are as described below for other procedures. The shaft 118 has an outer diameter K of 0.022 inch. The catheter 110 has an overall usable length of approximately 46 cm and is used to dilate an ostium after failed DCR as described above, except that the catheter can be inserted directly into the angiocath sleeve, or can be used immediately after the metal probe has been inserted and withdrawn.

It is desirable for a catheter according to the invention to have a lubricious coating to facilitate insertion of the catheter into the lacrimal system. A silicone coating bonded to the shaft of the catheter is preferred, such as the coating described in U.S. Ser. No. 370,917, filed Jun. 23, 1989, which is incorporated herein by reference. Alternatively, a topical coating of silicone oil can be applied before insertion. One such topical lubricant is Dow Corning 360 medical fluid available from Dow Corning Corp.

Figure 7:
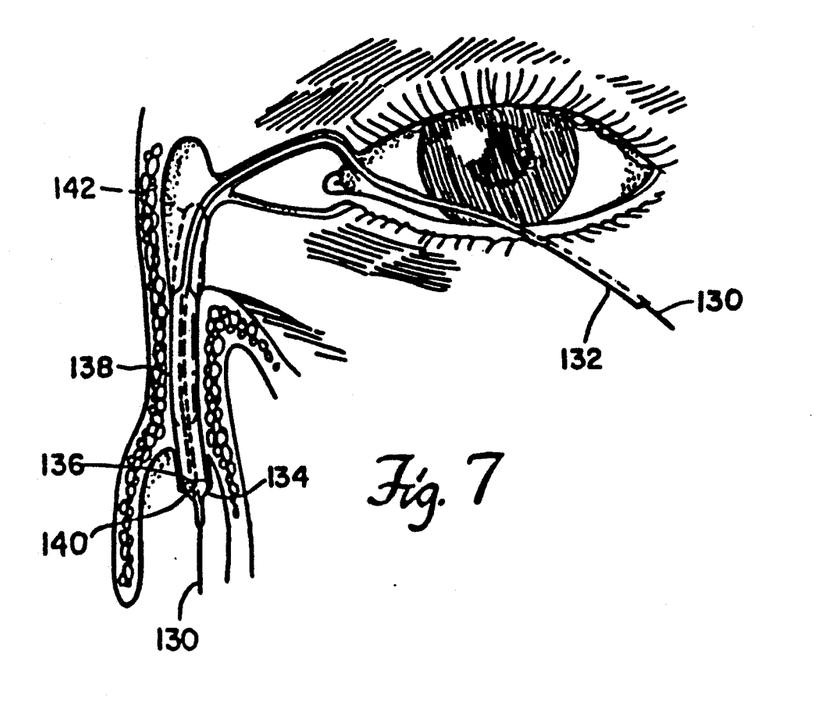
FIG. 7 is a schematic view of the method according to the invention of dilatating the nasolacrimal duct.

A method for treating an obstructed nasolacrimal duct is shown in FIG. 7. A guide wire 130 and catheter 132 are inserted as described above, except that the second opening through which the guide wire 130 and the catheter 132 emerge is the natural opening 136 of the nasolacrimal duct 138 rather than an artificially created ostium. A balloon 134 is advanced so that the full-diameter center region of the balloon is visible distal to the opening 136. Preferably, an inflation marker 140 is positioned 4-6 mm proximal to the distal end of the center region for alignment with the opening 136. The balloon 134 is preferably 25-30 mm in length and 3.5-4.5 mm in diameter for dilatation of an adult nasolacrimal duct which is typically approximately 17 mm in length. If a shorter balloon is used, a 2-step dilatation procedure is performed in which the balloon is first positioned as shown in FIG. 7, inflated to 10 bars for 8 minutes, and deflated and pulled slightly proximally such that the punctum is aligned midway between two marks which are 9-11 mm and 14-16 mm, preferably 10 mm and 15 mm, respectively, proximal to the proximal end of the center region of the balloon 134. The position of the balloon upon the second dilatation is indicated in phantom by dashed line 142 during the second dilatation procedure. Alternatively, particularly when a larger diameter balloon is required, the catheter 132 can be directed in a retrograde manner through the opening 136 and then into the nasolacrimal duct 138. The distal end of the catheter 132 in this construction extends at least 15 mm beyond the distal end of the center region so that two insertion markers can be placed at 10 mm and 15 mm distal to the distal end of the center region for alignment with the punctum during the retrograde technique. Additionally, a passage can be established through the medial wall of the lacrimal sac by surgically creating such an opening as described above for DCR.

For treatment of a child, especially 1-2 years old, a smaller, shorter balloon of 2-4 mm diameter and 15-20 mm length appears to be desirable.

Figure 8:
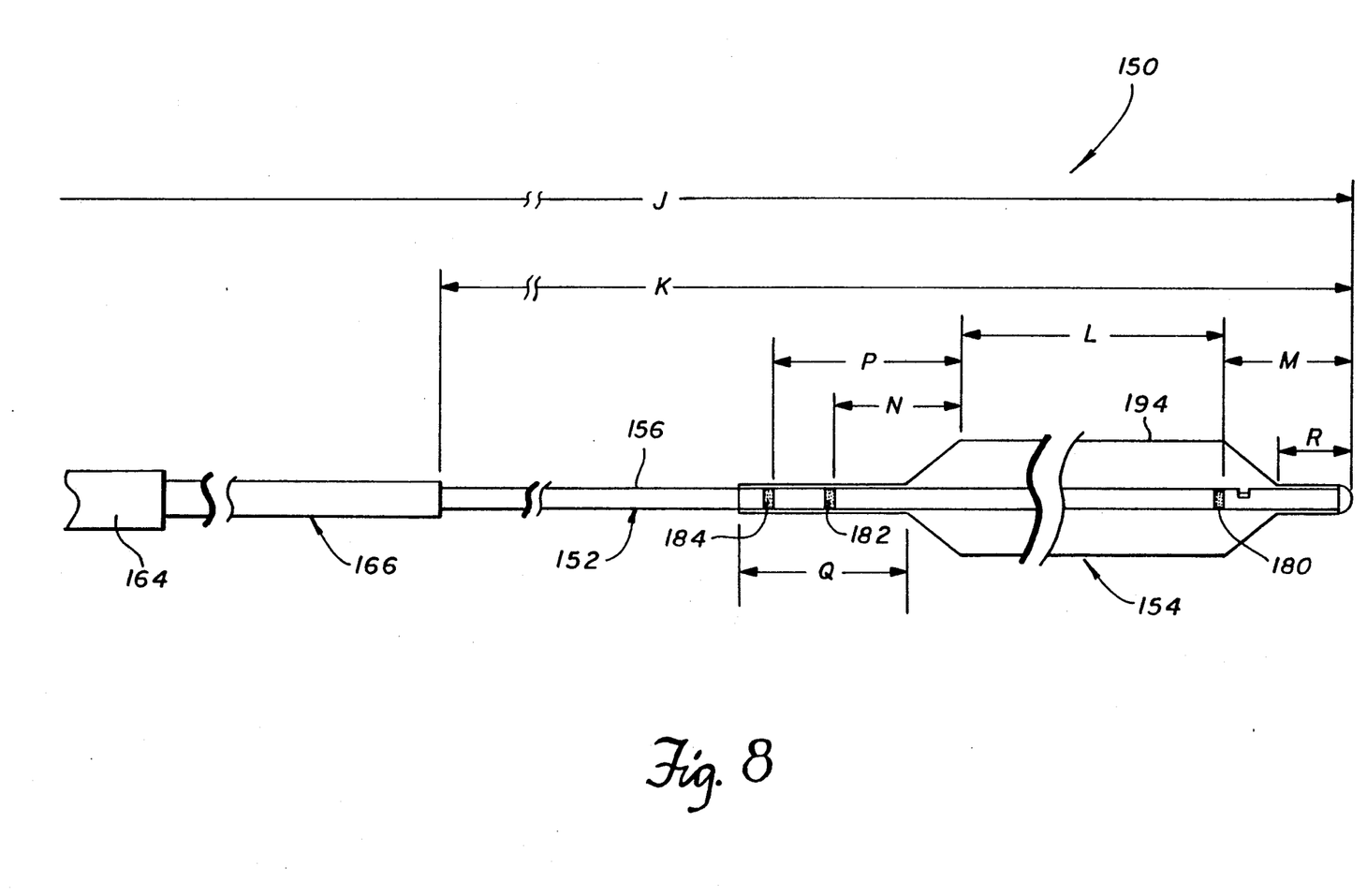
FIG. 8 is a schematic view of a dilatation catheter according to the present invention.
Figures 9A, 9B, 10:
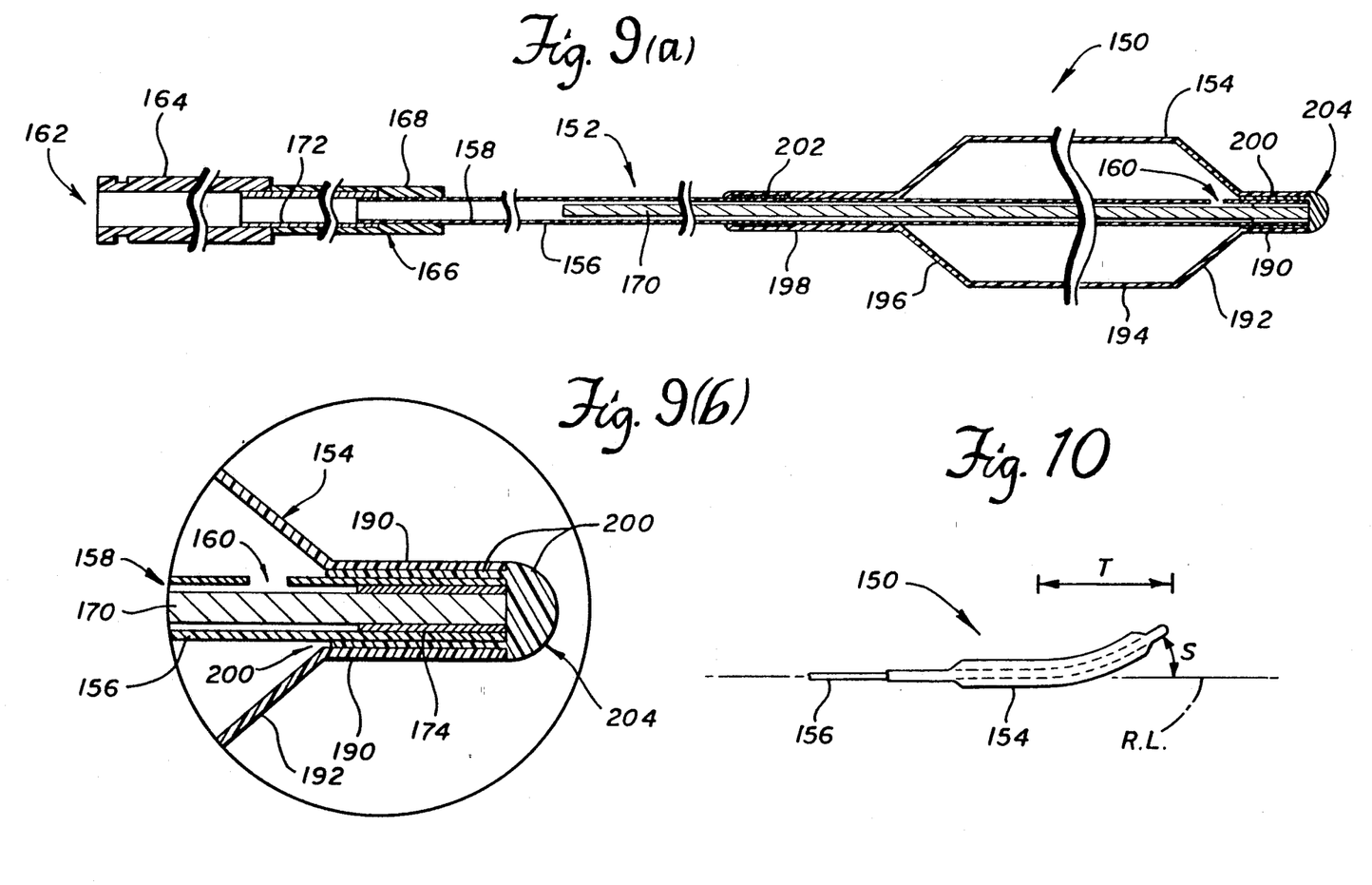

A dilatation catheter 150 according to the present invention is shown in FIGS. 8-10. The catheter 150 is constructed to simulate a standard opthalmic probe in stiffness, in terms of both column strength and resistance to lateral bending. The catheter 150 has sufficient flexibility to enable it to conform to the contours of the lacrimal system, while having a sufficient stiffness (both columnar and flexural) to prevent kinking or excessive bending which may defeat insertion through a constricted portion of the lacrimal system. Further, it is desirable to provide an initially straight, noncurved catheter whose curvature can be altered as desired by a physician. Presently, an opthomologist may vary the curvature of an opthalmic probe between zero to thirty degrees to follow the curvature of the lacrimal system. The dilatation catheter 150 includes a curve retention element 170, described in more detail below, which allows a physician to impart a selected curvature to the dilatation catheter 150.

The dilatation catheter 150 includes a catheter body 152 which carries a dilatation balloon 154. The main portion of the catheter body 152 is formed of hollow tube 156 which defines an inflation lumen 158, FIG. 9, having a distal end communicating through port 160 with the interior of the balloon 154, and having a proximal end 162 which is accessible through luer 164 and reinforcing sleeve 166. The reinforcing sleeve 166 is formed of a polyolefin strain relief section 168 and an inner metal tube 170 as described in more detail below.

A key feature of the improved dilatation catheter 150 is the curve retention element 170 which enables the catheter 150 to retain a curved shape after mechanical force is applied to it, and enables the catheter 150 to simulate the flexibility and column stiffness of an opthalmic probe. The curve retention element 170 serves several functions in addition to maintaining a curved shape after it is bent beyond its yield point, as discussed below. The element 170 also increases the columnar and flexural stiffness of the distal portion of the catheter 150, which enhances its ability to be forced through a constricted portion of the lacrimal system and to more closely simulate an opthalmic probe. Further, the curve retention element 170 supports the tube 156 in the region of the port 160 where it is weakened by the presence of the port 160. Metal is a preferred material for the curve retention element 170 because it possesses both strength and flexibility. Medical grade 304 stainless steel wire appears to the most desirable material.

One technigue of using the dilatation catheter 150 to dilatate the nasolacrimal duct is described as follows. The nose of a patient is packed in the region of the inferior meateus with a ½ inch by 3 inch cottonoid soaked in a solution of half and half 4% lidocaine and 0.5% phenylephrine. A Q-tip cotton swab soaked in the same solution is placed against the roof of the nose posteriorly and at its midpoint. A half and half mixture of 2% lidocaine with epinephrine and 0.75% Marcaine with Wydase then is injected along the medial orbit to block the anterior ethmoidal and infratrochlear nerves. The nasal packings are removed at the beginning of the insertion procedure.

The distal portion of a number 00 Bowman probe is bent gently to create a curve between 0°-30°, typically 15°-20°. The length of the curved distal portion is typically between 15-40 mm, preferably approximately 25 mm. The bent probe then is brought through the superior canaliculus into the lacrimal sac and then the distal end of the probe is oriented vertically. The probe is brought down through the nasolacrimal duct into the nose. The distal end of the probe is observed in the nose using a nasopharyngoscope. The probe is then withdrawn.

The dilatation catheter 150 then is bent along the distal portion represented by arrow T, FIG. 10, to angle S, relative to reference line RL. Region T is approximately 15-40 mm in length, preferably approximately 25 mm, and angle S is between 0°-30°, preferably 15°-20°. In other words, the dilatation catheter 150 is bent to simulate the curvature of the opthalmic probe. The curvature accomodates curves within the lacrimal system and also enables the proximal portion of the catheter 150 to remain clear of the eyebrows and forehead of the patient. After a selected curved shape is obtained, the distal end of the catheter 150 is inserted through the superior canaliculus into the lacrimal sac. The distal tip then is oriented vertically and brought down the nasolacrimal duct into the nose. The distal tip of the catheter 150 is visualized in the nose with the nasopharyngoscope so that the distal marker 180, FIG. 8, is observed. The punctum is aligned midway between proximal markers 182 and 184. The balloon 154 is mildly dilated to 1-2 bars and pulled slightly proximally until resistance is felt at the level of the common canaliculus. The balloon 154 then is pushed distal to the common canaliculus by 1-2 mm, and is fully dilated to ten bars for ten minutes. The balloon 154 is inflated and dilatation is repeated for 5-8 minutes. Subsequently, the balloon 154 is deflated and removed completely from the lacrimal system. Irrigation then is performed through the lacrimal system into the nose with fluorescein stained saline to confirm passage of the fluid into the nose.

The details of the construction of a catheter 150 are as follows. The proximal end of the catheter 150 is assembled by inserting the proximal end of the main tube 156 into the distal end of the proximal tube 172 by approximately 5-10 mm and then brazing the tubes together. The tube 156 preferably is a stainless steel hypotube having an outer diameter of 0.022 inch, an inner diameter of 0.017 inch, and a length of 49 cm. The proximal tube 172 is a stainless steel hypotube having an outer diameter of 0.036 inch, an inner diameter of 0.024 inch, and a length of 6 cm. Approximately 1 cm of the proximal end of the tube 172 is inserted into a mold, and the luer 164 is formed by injection molding over it. The interior taper of the luer is not shown although, in the illustrative embodiment, the inner diameter narrows from a diameter at its proximal end of 0.170 inch to a diameter which matches that of the tube 172. A strain relief section 168 is formed of polyolefin having an outer diameter of 0.060 inch, an inner diameter of 0.036 inch, and a length of 7 cm. The section 168 increases the strength at the transition between the main shaft 156 and the luer 164, and enhances its visual appearance by covering the brazed joint between the tubes 156 and 172.

The distal portion of the catheter 150 is formed by inserting temporarily a discardable wire segment having a diameter of 0.012 inch into the distal end of the tube 156 (which at this construction stage lacks all other illustrated distal features). A transverse slot is cut in the tube 156 approximately 8 mm from its distal end to form the port 160. The slot extends in depth to approximately ⅓ of the diameter of the tube 156. A wire wheel is used to remove any burrs, and the discardable core wire is removed and discarded. The curve retaining element 170 is established by selecting a stainless steel wire having a diameter of 0.010 inch and a length of 17 cm±5 cm in length and inserting it through the distal end of the tube 156, leaving approximately 1 mm projecting distally from the distal end of the tube 156. The element 170 is then brazed or soldered to the tube 156 as represented by solder 174, shown in more detail in FIG. 9a. The remainder of the element 170 is left unattached for ease of manufacture and to insure patency of the lumen 158 to port 160. The port 160 then is covered temporarily with shrink tubing and air is forced through luer 164 to test the integrity of the solder 174. If the lumen 158 is completely occluded at the joint formed by the solder 174, the joint is successful. The shrink tubing then is removed.

It is desirable for the catheter 150 to have a column strength and resistance to lateral bending similar to that of an opthalmic probe. A catheter according to the invention having the dimensions of the illustrative embodiment was tested in an Olsen Stiffness Tester to compare the flexure of the catheter with a Guibor caniliculus probe from a Guibor canaliculus intubation silicone set, catalog no. 9045, available from Concept Incorporated, Largo, Fla. The Olsen Stiffness Tester is available from Tinius Olsen Testing Machine Co., Inc., Willow Grove, Pa. The test was conducted according to ASTM designation D747-83, "Standard Test Method for STIFFNESS OF PLASTICS BY MEANS OF A CANTILEVER BEAM", volume 08.01 (1986). The following stiffness in flexure was measured for the catheter and a Guibor probe:

| Angle (Degrees) | Stiffness (PSI) of Catheter | Stiffness (PSI) of Probe |
| --- | --- | --- |
| 10 | $20.1 \times 10^6$ | $20.6 \times 10^6$ |
| 20 | $17.8 \times 10^6$ | $18.0 \times 10^6$ |
| 30 | $15.0 \times 10^6$ | $15.5 \times 10^6$ |

A curved shape is retained by an opthalmic probe and a catheter according to the present invention when the elastic limit is exceeded and the material is placed in the "plastic" region. The ASTM test method does not distinguish or separate the elastic and plastic components, but instead obtains an apparent value as shown above. Preferably, the dilatation catheter according to the present invention has a stiffness in flexure of 14.2 to 21.4 $\times 10^6$ PSI at an angle of twenty degrees.

A distal balloon marker 180, FIG. 8, is established by applying permanent black ink approximately 10 mm proximal of the distal end of the tube 156 as shown by length M. The visually perceivable marker 180 corresponds with the distal end of the center region of the balloon 154 after it is installed, as described below. For dilatation of the nasolacrimal duct, it is preferable for the marker 180 to be aligned with the center region 194 as shown in FIG. 8, that is, to be located 0 mm proximal (or distal) to the distal end of the center region 194 for observation in the nose using a nasopharyngoscope. It is desirable for the marker 180 to be located 0-6 mm proximal or distal to the distal end of the center region 194, and more desirable to be 0-6 mm proximal to the distal end of the center region 194 so that the opthomologist can determine precisely that the entire passage into the nose will be dilatated fully by the center region 194.

Markers 182 and 184 are established by applying 1 mm ink bands at approximately 50 and 55 mm from the distal end of the tube 156. The markers 182, 184 are 10 and 15 mm (represented by lengths P and N), respectively, proximal to the proximal end of the center region of the balloon 154 after it is installed.

A balloon 154 preferably formed of polyethylene terephthalate and having a length of approximately 10-15 mm for use in a child and 30 mm maximum for use in an adult. Different balloon lengths and diameters are desired for dilatation of other portions of the lacrimal system as described above in relation to the invention of the parent application; the above described balloon length and diameter apply to the catheter of the present invention. The diameter of the balloon 154 typically ranges between 3-6 mm. The illustrated balloon 154 has a diameter of 3.5 mm and a center region 194 having a length of 30 mm (length L). As shown in FIG. 9, the balloon 154 has a distal neck 190 which is approximately 1-10 mm in length, preferably 1-3 mm, and a distal tapered region 192, a center region 194, a proximal tapered region 196, and a proximal neck 198 which is approximately 15 mm in length (length Q). During installation, both necks 198 and 190 are cleaned in acetone and are plasma etched for eight minutes at 300 watts at 0.25 torr. The balloon is placed over the distal end of the tube 156 to align the distal end of distal neck 190 with the distal end of the tube 156. An ultraviolet-curing adhesive such as acrylic acid and methacrylic ester. An acceptable adhesive is UV 350 available from Loctite Corporation. The adhesive is applied to the distal end of the distal neck 190 and the proximal end of the proximal neck 198 to form bonds 200 and 202, respectively. Sufficient adhesive is applied at the distal end to form a domed tip 204, shown in greater detail in FIG. 9a. The adhesive is applied to the balloon necks 190, 198 using a small mandrel such as a wire approximately 0.010-0.014 inch in diameter. The adhesive wicks into the necks due to capillary action. The adhesive 200, 202 and balloon 154 are exposed to an ultraviolet light source such as source model no. ELC600 available from Electrolite Corporation. After the initial curing of the bonds, voids may be present. A second application of adhesive is applied in the same manner. At this time, the rounded, dome-shaped tip 204 is formed from the adhesive 200. The adhesive 200, 202 and the balloon 154 are again exposed to the ultraviolet light to cure the additional adhesive. The completed catheter has a usable length K (distal to section 166) of 46 cm±5 cm and an overall length J of 56 cm±7 cm.

A dilatation catheter and method according to the invention can also be used to dilate a narrowed conjunctivodacryocystorhinostomy (CDCR) tract through which a pyrex tube has been placed, or for creation of a new tract after an incision has been made to create such a passage leading from the eye into the nose while bypassing the canaliculi. A metal probe or other instrument is brought through the CDCR from the eye directly into the nose, and then withdrawn. It is not necessary to use an angiocath when a dilatation catheter according to the present invention is used, which avoids additional trauma to the nasal cavity that may be formed by the angiocath. The catheter is inserted along the path of the probe. The balloon is preferably 4-6 mm in diameter and 10-20 mm in length so that the proximal end of the center region of the balloon remains exterior to the opening by the eye and the distal end of the center region protrudes into the nose. The balloon is inflated at ten bars pressure for two eight-minute periods. The balloon is then withdrawn. Alternatively, the balloon may be brought in a retrograde manner from the nose side into the CDCR passage. In either method, a standard stent later may be placed to maintain patency.

Obstruction of a canaliculus can be similarly treated using a balloon having a diameter of 2-4 mm and a length of 15-20 mm for dilating the entire canalicular passage, or a shorter length of 4-8 mm for dilating a selected region of the canaliculus. If a DCR has previously been performed, one end of the center region projects external to the punctum while the other end of the center region projects exterior to or is visible through the ostium. If an ostium has not been previously created, the interior end of the balloon resides within the nasolacrimal duct. In the latter case, it is desirable to have two insertion markers spaced 9-11 and 14-16 mm, preferably 10 mm and 15 mm, respectively, from the interior end of the center region for alignment relative to the punctum. In other words, if the catheter is directed from the eye into the nasolacrimal duct, one insertion marker is located 10 mm proximal to the distal end of the center region and a second marker is located 15 mm proximal to the distal end of the center region. The markers will be spaced distal to the distal end of the center region when the catheter is brought in a retrograde manner through the nasolacrimal duct and into the canaliculus.

In an extremely obstructed canaliculus, an ostium is created through DCR and a sterile safety pin or other sharp instrument is passed through the lacrimal sac and into the canaliculus to create a new passage or opening. Standard silicone intubation may be installed after dilatation through the canalicular system at the completion of the procedure.

Dilatation can also be performed of the punctum. A balloon is placed through the entire lacrimal system but brought through the punctum so that the ends of the center region project on either side of the punctum. A probe is usually not required and the catheter is simply inserted into the punctum and slightly into the canaliculus.

Although specific features of the invention are shown in some drawings and not in others, it is for convenience only as each feature may be combined with any or all of the other features in accordance with the invention.

It should be understood, however, that the foregoing description of the invention is intended merely to be illustrative thereof and that other modifications, embodiments, and equivalents may be apparent to those skilled in the art without departing from its spirit.

Having thus described the invention what we desire to secure by Letters Patent is:

We claim:

1. A method of restoring patency to an obstructed portion of the lacrimal system of a patient, comprising:
   providing a catheter including:
      catheter body having a proximal end and a distal end;
      an inflatable member formed of noncompliant material and disposed proximate to the distal end of the catheter body, the inflatable member having when inflated a center region, a distal tapered region and a proximal tapered region, the distal region attached to the distal end of the center region and the proximal tapered region attached to the proximal end of the center region;
      means, carried by the catheter body near the distal end of the catheter body, for retaining a curved shape after mechanical force is applied to it, the curved shape enabling the catheter to be more readily inserted through the lacrimal system to access the obstructed portion; and
      at least one visually perceivable marker having a known spaced relationship from one of the distal end and the proximal end of the center region for enabling alignment of the inflatable member with the obstructed portion of the lacrimal system to be dilated;
   inserting the catheter into the lacrimal system;
   positioning the inflatable member in the obstructed portion of the lacrimal system by aligning the marker relative to an opening into the lacrimal system; and
   inflating the inflatable member to dilate the obstructed portion to restore patency to the lacrimal system.

2. The method of claim 1 in which inserting the catheter includes applying mechanical force to the means for retaining to impart a selected curved shape to the catheter.

3. The method of claim 1 further including initially passing a probe through the lacrimal system to determine a path between the first and second openings through the obstruction.

4. The method of claim 3 further including bending a distal portion of the probe to a selected curved shape to facilitate insertion through the lacrimal system.

5. The method of claim 4 further including bending a portion of the means for retaining so that the catheter assumes a curved shape substantially similar to the selected curved shape of the probe.

6. The method of claim 1 wherein the catheter is inserted through a punctum and associated canaliculus, and then through an ostium formed between the nose and the lacrimal sac, and a first visually perceivable marker is spaced 9-13 mm proximal to the proximal end of the center region, and positioning the inflatable member includes aligning the first marker relative to the punctum.

7. The method of claim 6 wherein the inflatable member is translucent, a second visually perceivable marker is located beneath the inflatable member at a distance of 0-6 mm distal to the proximal end of the center region, and positioning further includes aligning the second marker relative to the ostium.

8. The method of claim 1 wherein the catheter is inserted through an ostium formed between the nose and the lacrimal sac, and then through a canaliculus and its associated punctum, and a first visually perceivable marker is spaced 9-13 mm distal to the distal end of the center region, and positioning the inflatable member includes aligning the first marker relative to the punctum.

9. The method of claim 8 wherein the inflatable member is translucent, a second visually perceivable marker is located beneath the inflatable member at a distance of 0-6 mm proximal to the distal end of the center region, and positioning further includes aligning the second marker relative to the ostium.

10. The method of claim 1 wherein the catheter is inserted through a punctum and associated canaliculus, and then through the nasolacrimal duct, and the inflatable member is translucent, a first visually perceivable marker is located beneath the inflatable member at a distance of 0-6 mm proximal to the distal end of the center region, and positioning further includes aligning the first marker relative to the opening of the nasolacrimal duct into the nose.

11. The method of claim 10 wherein a second visually perceivable marker is spaced 9-16 mm proximal to the proximal end of the center region, and positioning the inflatable member includes aligning the second marker relative to the punctum.

12. The method of claim 11 wherein the second marker is located 9-11 mm proximal to the proximal end of the center region, and the catheter further includes a third marker located 14-16 mm proximal to the proximal end of the center region, and positioning the inflatable member includes aligning the second and third markers relative to the punctum.

13. The method of claim 12 in which a first dilatation is performed after the first marker is aligned relative to the opening of the nasolacrimal duct, and a second dilatation is performed after aligning the second and third markers relative to the punctum.

14. The method of claim 1 wherein the catheter is inserted through a punctum and associated canaliculus for dilatation of the canaliculus, and a first visually perceivable marker is spaced 9-16 mm proximal to the distal end of the center region, and positioning the inflatable member includes aligning the first marker relative to the punctum.

15. The method of claim 1 wherein the provided catheter includes a lubricious coating to facilitate inserting the catheter into the lacrimal system.

16. The method of claim 15 further including topically applying the coating to the catheter body and the inflatable member.

17. A catheter for dilating an obstructed portion of the lacrimal system of a patient, comprising:
   a catheter body having a proximal end and a distal end;
   an inflatable member disposed proximate to said distal end of said catheter body, said inflatable member having when inflated a center region, a distal tapered region and a proximal tapered region, said distal region attached to a distal end of said center region and said proximal tapered region attached to a proximal end of said center region;, and
   fixed means, carried by said catheter body and located only near said distal end of said catheter body, for retaining a permanent curved shape after mechanical force is applied to it, the curved shape enabling said catheter to be more readily inserted through the lacrimal system to access the obstructed portion.

18. The catheter of claim 17 in which said catheter body defines an inflation lumen having a distal opening communicating with said inflatable member to enable inflation and deflation of said inflatable member.

19. The catheter of claim 18 in which said fixed means for retaining occupies a distal portion of said inflation lumen without occluding said lumen.

20. The catheter of claim 19 in which said fixed means for retaining includes a metal wire attached to said catheter body distal to said distal opening of said inflation lumen.

21. The catheter of claim 17 in which said fixed means for retaining retains a curved shape after sufficient mechanical force is applied to exceed its elastic limit.

22. The catheter of claim 17 in which a distal portion of said catheter has a stiffness in flexure of between 14.2 to $21.4 \times 10^6$ pounds per square inch as measured on an Olsen Stiffness Tester according to ASTM D747-83.

23. The catheter of claim 17 in which the curved shape exhibits an angle of between one and thirty degrees.

24. The catheter of claim 17 in which said distal end of said catheter includes a rounded distal tip formed of cured adhesive.

25. The catheter of claim 17 in which said means for retaining is a metal element.

26. The catheter of claim 25 in which said metal element is a wire formed of stainless steel and said catheter body includes a hollow metal tube.

27. The catheter of claim 17 further including at least one visually perceivable marker having a known spaced relationship from one of said distal end and said proximal end of said center region for enabling alignment of said inflatable member with the obstructed portion of the lacrimal system to be dilated.

28. The catheter of claim 27 wherein a first visually perceivable marker is spaced 9-13 mm proximal to said proximal end of said center region for alignment relative to a punctum of the patient.

29. The catheter of claim 28 wherein said inflatable member is translucent and a second visually perceivable marker is located beneath said inflatable member at a distance of 0-6 mm distal to said proximal end of said center region for alignment relative to an ostium formed between the nose and the lacrimal sac of the patient.

30. The catheter of claim 29 in which said inflatable member has a diameter of 3-6 mm when inflated.

31. The catheter of claim 30 in which said inflatable member has a length of 5-10 mm.

32. The catheter of claim 27 wherein a first visually perceivable marker is spaced 9-13 mm distal to said distal end of said center region for alignment with a punctum of the patient.

33. The catheter of claim 32 wherein said inflatable member is translucent and a second visually perceivable marker is located beneath said inflatable member at a distance of 0-6 mm proximal to said distal end of said center region for alignment relative to an ostium formed between the nose and the lacrimal sac of the patient.

34. The catheter of claim 27 wherein said inflatable member is translucent and a first visually perceivable marker is located beneath said inflatable member a distance of 0-6 mm proximal to said distal end of said center region for alignment relative to the opening of the nasolacrimal duct into the nose.

35. The catheter of claim 34 wherein a second visually perceivable marker is spaced 9-16 mm proximal to said proximal end of said center region for alignment relative to a punctum of a patient.

36. The catheter of claim 35 wherein said inflatable member has a diameter when inflated of 2-5 mm.

37. The catheter of claim 36 wherein said inflatable member has a length of 15-30 mm.

38. The catheter of claim 36 wherein said second marker is located 9-11 mm from said proximal end of said center region and said catheter further includes a third visually perceivable marker located 14-16 mm proximal to said proximal end of said center region.

39. The catheter of claim 34 wherein said inflatable member has a diameter of 2-4 mm when inflated.

40. The catheter of claim 27 wherein a first visually-perceivable marker is spaced 9-16 mm proximal to said distal end of said center region for alignment relative to a punctum of the patient for dilatation of a canaliculus.

41. The catheter of claim 17 further including a lubricious coating disposed on said catheter body to facilitate inserting said catheter into the lacrimal system.

42. A catheter for dilating an obstructed portion of the lacrimal system of a patient, comprising:
   a catheter body having a proximal end and a distal end;
   an inflatable member formed of noncompliant material and disposed proximate to the distal end of said catheter body, said inflatable member having when inflated a center region, a distal tapered region and a proximal tapered region, said distal region attached to a distal end of said center region and said proximal tapered region attached to a proximal end of said center region;
   said catheter body defining an inflation lumen having a proximal opening near said proximal end of said catheter body and having a distal opening communicating with said inflatable member; and
   fixed means, carried by said catheter body and located only near said distal end of said catheter body, for increasing the stiffness of said catheter body to resist kinking, while enabling said catheter body to be permanently bend to curved shape to enable said catheter to be more readily inserted through the lacrimal system to access the obstructed portion.

43. The catheter of claim 42 om which said fixed means for increasing the stiffness includes a metal element carried within a distal portion of said catheter body.

44. The catheter of claim 43 in which said metal element retains a selected curved shape after sufficient mechanical force is applied to it.

45. The catheter of claim 42 further including at least one visually perceivable dilatation marker disposed within said center region of said inflatable member for enabling alignment of said inflatable member with the obstructed portion of the lacrimal system to be dilated.

46. The catheter of claim 45 further including at least one visually perceivable insertion marker spaced from one of said distal end and said proximal end of said center region for enabling positioning of said inflatable member relative to an opening into the lacrimal system.

* * * * *